(12) United States Patent
Shinden

(10) Patent No.: US 11,197,646 B2
(45) Date of Patent: Dec. 14, 2021

(54) X-RAY IMAGING SYSTEM

(71) Applicant: Konica Minolta, Inc., Tokyo (JP)

(72) Inventor: Yuko Shinden, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 157 days.

(21) Appl. No.: 15/935,684

(22) Filed: Mar. 26, 2018

(65) Prior Publication Data

US 2018/0279977 A1 Oct. 4, 2018

(30) Foreign Application Priority Data

Mar. 29, 2017 (JP) .............................. JP2017-064717

(51) Int. Cl.
*G21K 1/06* (2006.01)
*A61B 6/00* (2006.01)
*G06T 11/00* (2006.01)

(52) U.S. Cl.
CPC .......... *A61B 6/4035* (2013.01); *A61B 6/4028* (2013.01); *A61B 6/42* (2013.01);
(Continued)

(58) Field of Classification Search
CPC ... A61B 6/4233; A61B 6/4241; A61B 6/4266; A61B 6/4275
See application file for complete search history.

(56) References Cited

U.S. PATENT DOCUMENTS

2013/0094625 A1* 4/2013 Huang .................. A61B 6/484
378/6

2013/0201198 A1* 8/2013 Nagatsuka ............. A61B 6/463
345/581
(Continued)

FOREIGN PATENT DOCUMENTS

JP 3547248 B2 7/2004
JP 2014090967 A 5/2014
(Continued)

OTHER PUBLICATIONS

Notice of Reasons for Refusal issued in corresponding Japanese Patent Application No. 2017-064717, dated Mar. 3, 2020, with translation (4 pages).

*Primary Examiner* — David P Porta
*Assistant Examiner* — Mamadou Faye
(74) *Attorney, Agent, or Firm* — Osha Bergman Watanabe & Burton LLP

(57) ABSTRACT

An X-ray imaging system includes an X-ray Talbot imaging device and an image processing device. The image processing device includes a hardware processor and a display. The hardware processor generates multiple types of reconstructed images based on each of moire images having different subject set angles captured by the X-ray Talbot imaging device; groups the reconstructed images by subject set angle and by type; detects, in each reconstructed image, a grating direction of the gratings and the subject set angle relevant to the grating direction; matches an image direction in each of the grouped reconstructed images with a reference direction based on the grating direction and the subject set angle; performs a same image adjustment process on the grouped reconstructed images; and causes the display to display the reconstructed images grouped by subject set angle or by type.

5 Claims, 8 Drawing Sheets

(52) U.S. Cl.
CPC ............ *A61B 6/463* (2013.01); *A61B 6/5235* (2013.01); *G06T 11/005* (2013.01); *G06T 11/006* (2013.01)

(56) References Cited

U.S. PATENT DOCUMENTS

| | | | |
|---|---|---|---|
| 2016/0042533 A1* | 2/2016 | Kiyohara | A61B 6/484 |
| | | | 382/103 |
| 2016/0310099 A1* | 10/2016 | Hamano | A61B 6/5235 |
| 2018/0226167 A1* | 8/2018 | Doki | G21K 1/025 |

FOREIGN PATENT DOCUMENTS

| | | |
|---|---|---|
| JP | 2015-198765 A | 11/2015 |
| JP | 2016150173 A | 8/2016 |
| WO | 2014167901 A1 | 10/2014 |

* cited by examiner

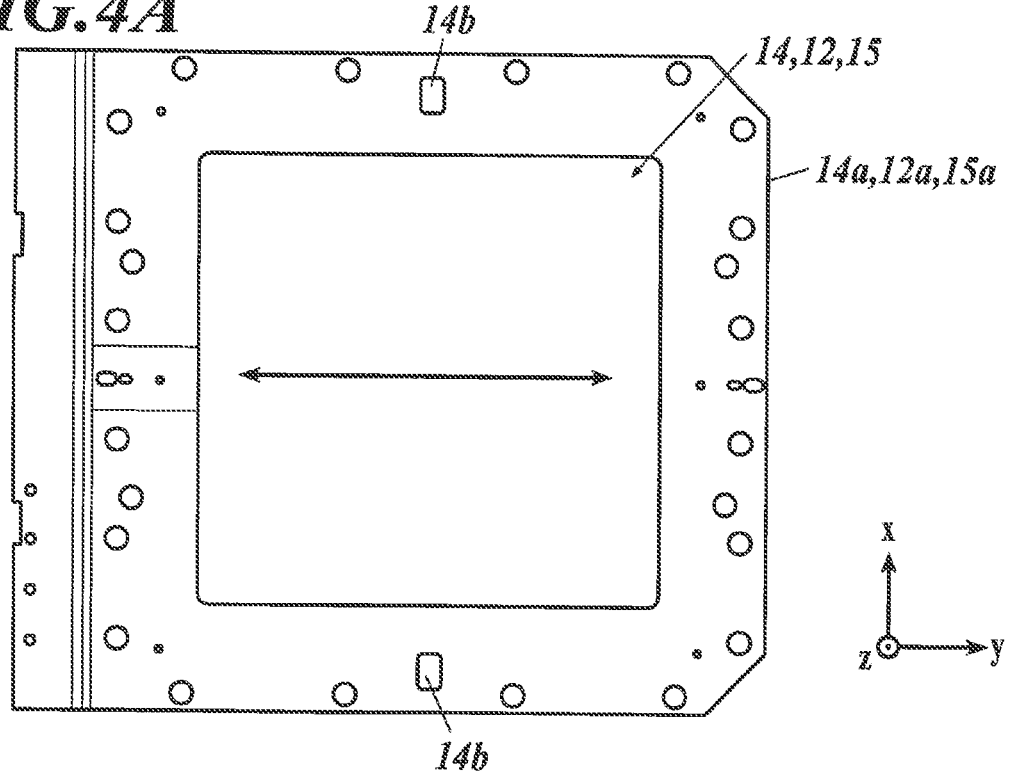
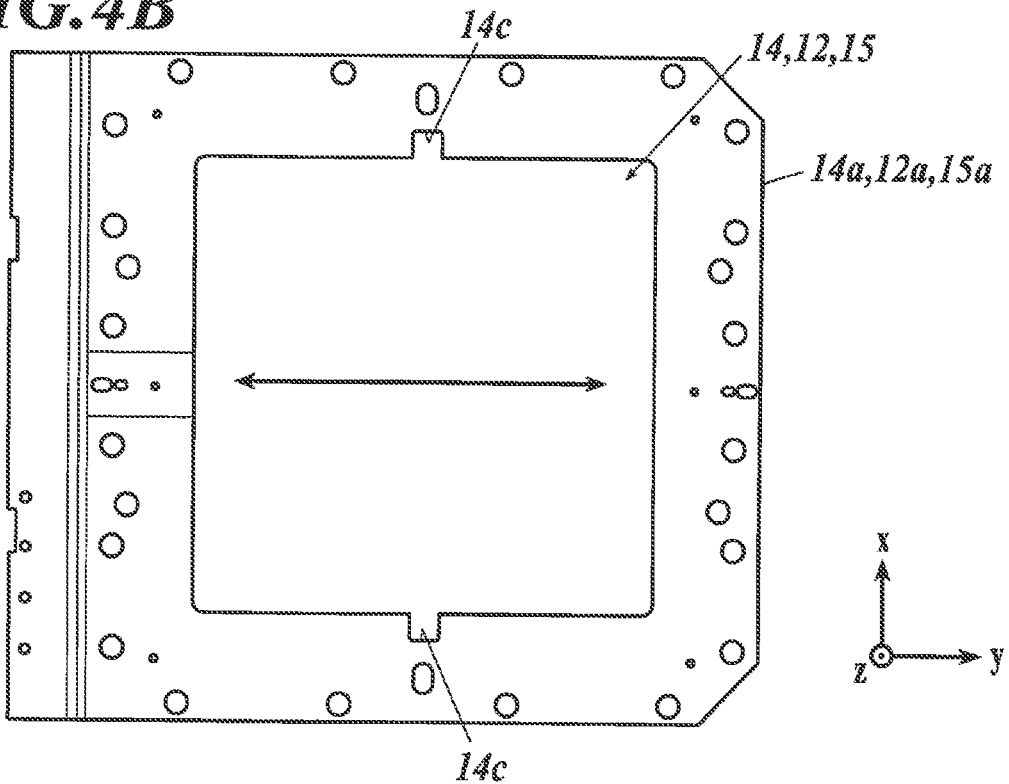

X-RAY IMAGING SYSTEM

CROSS-REFERENCE TO RELATED APPLICATIONS

The entire disclosure of Japanese Patent Application No. 2017-064717, filed on Mar. 29, 2017, is incorporated herein by reference in its entirety.

BACKGROUND

1. Technical Field

This invention relates to an X-ray imaging system.

2. Description of the Related Art

There have been known X-ray imaging devices each using a Talbot interferometer or a Talbot-Lau interferometer having one-dimensional gratings (hereinafter called X-ray Talbot imaging devices). At least three types of high-resolution reconstructed images that are absorption images, differential phase images and small angle scattering images can be obtained by an image processing device reconstructing moire images captured by an X-ray Talbot imaging device. In order to prevent, from happening, a situation where when at least three types of reconstructed images obtained by imaging with an X-ray Talbot imaging device using one-dimensional gratings are output to an external system, such as a PACS (Picture Archiving and Communication System), the reconstructed images get mixed with other reconstructed images, are lost or the like, there is disclosed in Japanese Patent Application Publication No. 2015-198765 (hereinafter Patent Document 1) a technique of grouping reconstructed images into image sets each constituted of at least three types of reconstructed images.

There is disclosed in Japanese Patent No. 3547248 (hereinafter Patent Document 2) an image display device that detects center positions in images obtained by imaging of a pair of subjects that are a right part and a left part, matches the center positions with one another, and displays the images on the same screen symmetrically. That is, the image display device disclosed in Patent Document 2 can display images obtained by imaging of a pair of subjects that are a right part and a left part back-to-back.

In the X-ray Talbot imaging device using one-dimensional gratings, an X-ray transmission amount varies according to a relative angle (subject set angle) of a subject to the gratings, and a visible image in a reconstructed image generated from X-rays varies according to the angle. By making use of this, the same site of a subject may be imaged multiple times at different subject set angles to accurately diagnose a predetermined site (i.e. the same site) of the subject.

If the same site of a subject is imaged multiple times at different subject set angles, it is possible, as with the technique disclosed in Patent Document 1, to group reconstructed images into image sets each constituted of at least three types of reconstructed images having the same subject set angle. However, the technique disclosed in Patent Document 1 does not associate reconstructed images having different subject set angles with one another and does not group such reconstructed images accordingly. Hence, if a user would like to compare reconstructed images of the same site of a subject having different subject set angles with one another for diagnosis, each time he/she would like to do, he/she needs to look for these reconstructed images, which is troublesome.

If reconstructed images of the same site of a subject having different subject set angles are retrieved and displayed in line on a screen of an image processing device, it is possible, by making use of the technique disclosed in Patent Document 2, to display the reconstructed images on the screen of the image processing device back-to-back. However, the technique disclosed in Patent Document 2 cannot match directions of these images with one another and display the images and also cannot perform image adjustment for image quality or the like on the images. Hence, if a user would like to compare reconstructed images of the same site of a subject having different subject set angles with one another for diagnosis, he/she needs to operate the reconstructed images separately, which is troublesome.

SUMMARY

One or more embodiments of the present invention matches subject directions in reconstructed images of one site (the same site) of a subject having different subject set angles with one another and displays the reconstructed images in line and performs the same image adjustment process for image quality or the like on the reconstructed images simultaneously, thereby increases diagnostic efficiency.

According to one or more embodiments of the present invention, there is provided an X-ray imaging system including: an X-ray Talbot imaging device that includes an X-ray source, a plurality of gratings and an X-ray detector disposed in line in an X-ray emission axis direction, and emits an X-ray from the X-ray source to the X-ray detector through a subject and the gratings and images (i.e., takes an image of) a same site of the subject multiple times at different subject set angles, thereby capturing, with the X-ray detector, moire images having the different subject set angles; and an image processing device that includes a hardware processor and a display, wherein the hardware processor: generates multiple types of reconstructed images based on each of the moire images having the different subject set angles captured by the X-ray Talbot imaging device; groups the multiple types of the reconstructed images by subject set angle and groups the multiple types of the reconstructed images by type; detects, in each of the multiple types of the reconstructed images, a grating direction of the gratings and the subject set angle relative to the grating direction; matches an image direction in each of the grouped reconstructed images with a reference direction based on the detected grating direction and the detected subject set angle; performs a same image adjustment process on the grouped reconstructed images; and causes the display to display the reconstructed images grouped by subject set angle or the reconstructed images grouped by type.

BRIEF DESCRIPTION OF THE DRAWINGS

The advantages and features provided by one or more embodiments of the present invention will become more fully understood from the detailed description given hereinbelow and the appended drawings which are given by way of illustration only, and thus are not intended as a definition of the limits of the present invention, wherein:

FIG. 4A shows a grating holder that holds a grating according to one or more embodiments of the present invention;

FIG. 4B shows a grating holder that holds a grating according to one or more embodiments of the present invention;

DETAILED DESCRIPTION OF EMBODIMENTS

Figure 1:
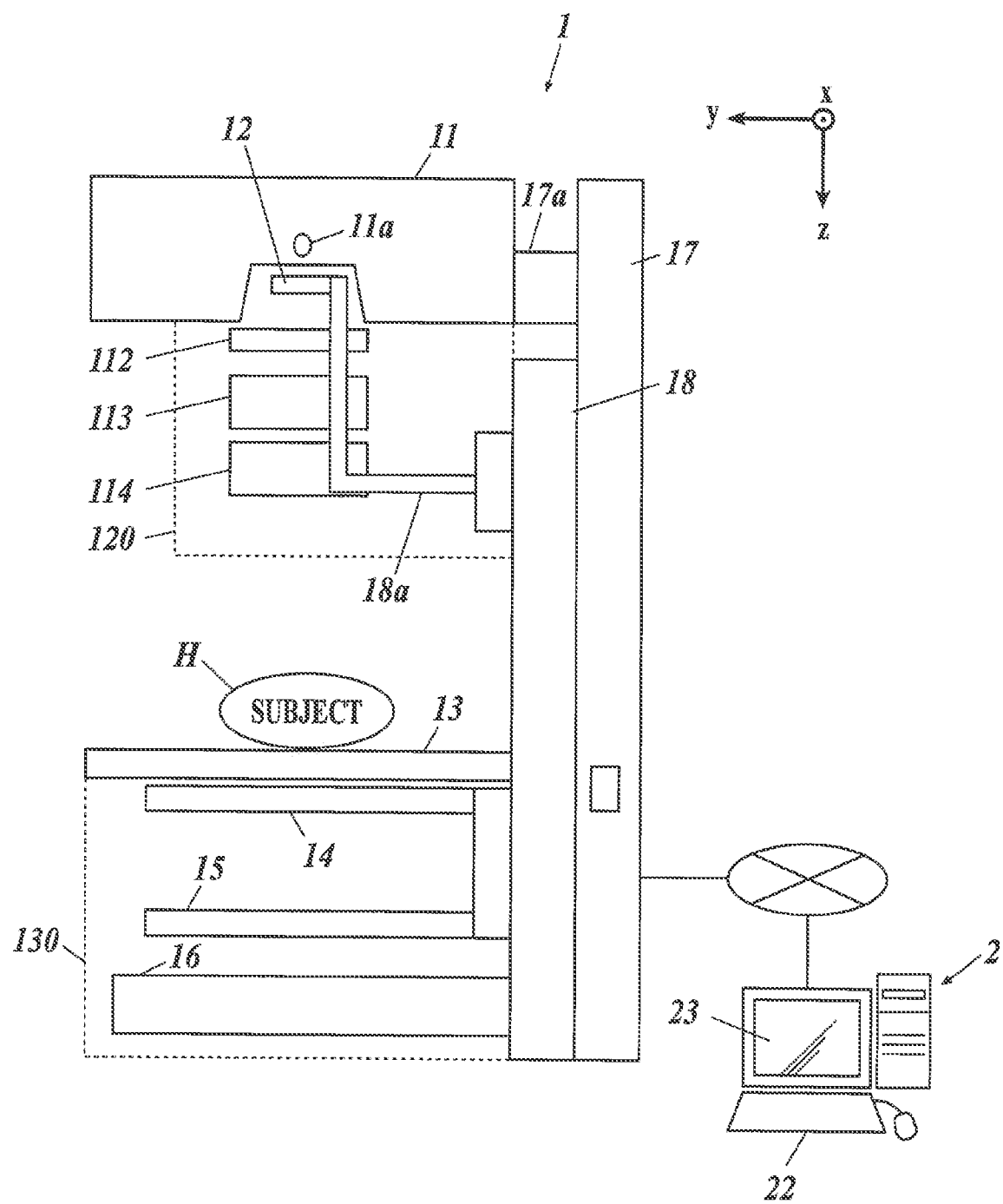
FIG. 1 is a schematic view showing the whole picture of an X-ray Talbot imaging device according to one or more embodiments of the present invention.

Hereinafter, embodiments of the present invention will be described with reference to the drawings. A variety of limitations that carry out the present invention are put on the embodiments described below. However, the technical scope of the present invention is not limited to the disclosed embodiments or illustrated examples.

In one or more embodiments of the present invention, an X-ray imaging system is described. In the X-ray imaging system, an X-ray Talbot imaging device 1 images the same site A of a subject H multiple times while changing the subject set angle (i.e. at different subject set angles), and an image processing device 2 generates, for each subject set angle, multiple types of reconstructed images on the basis of moire image(s) obtained/read by the X-ray Talbot imaging device 1.

As the X-ray Talbot imaging device 1, an X-ray Talbot imaging device using a Talbot-Lau interferometer having a source grating 12 (also called G0 grating), a first grating 14 (also called Ga grating) and a second grating 15 (also called G2 grating) is used. Alternatively, an X-ray Talbot imaging device using a Talbot interferometer having the first grating 14 and the second grating 15 only, without the source grating 12, may be used.

The subject H in one or more embodiments of the present invention is a finger joint part (site A). For example, if a finger has a rheumatic symptom, the joint part of the finger (site A) is imaged while the angle of the joint part is changed variously, so that the symptom can be more clearly observed. The subject H is not limited to the finger joint part (site A), and may be any site of the human body. The subject H is not even limited to the human body.

[X-ray Talbot Imaging Device]

FIG. 1 shows a schematic view showing the whole picture of the X-ray Talbot imaging device 1 of one or more embodiments of the present invention. The X-ray Talbot imaging device 1 includes, as shown in FIG. 1, an X-ray generator 11, the source grating 12, a subject table 13, the first grating 14, the second grating 15, an X-ray detector 16, a pole 17 and a base 18.

According to this X-ray Talbot imaging device 1, at least three types of images (called reconstructed images) can be reconstructed by: capturing moire images of the subject H placed at a predetermined position on the subject table 13 by a method based on principles of a fringe scanning method; or analyzing the moire images by Fourier transform method. The three types of images are absorption images (same as the ordinary X-ray absorption images) generated by imaging the average component of moire fringes in the moire images, differential phase images generated by imaging phase information on the moire fringes, and small angle scattering images generated by imaging visibility of the moire fringes. More types of images may be generated, for example, by reconstructing these three types of reconstructed images.

The fringe scanning method is a method for obtaining high-resolution reconstructed images by: performing imaging M times (M>2 for absorption images whereas M>3 for differential phase images and small angle scattering images, wherein M is a positive integer) while, for each imaging, moving one of gratings 1/M slit interval of the grating in a slit interval direction, thereby obtaining moire images; and performing reconstruction using the obtained moire images.

The Fourier transform method is a method for reconstructing and generating images, such as differential phase images, by: capturing one moire image with an X-ray Talbot imaging device in a state in which a subject is present; and performing Fourier transform on the moire image in image processing.

Hereinafter, principles common to Talbot interferometers and Talbot-Lau interferometer(s) are described with reference to FIG. 2.

Figure 2:
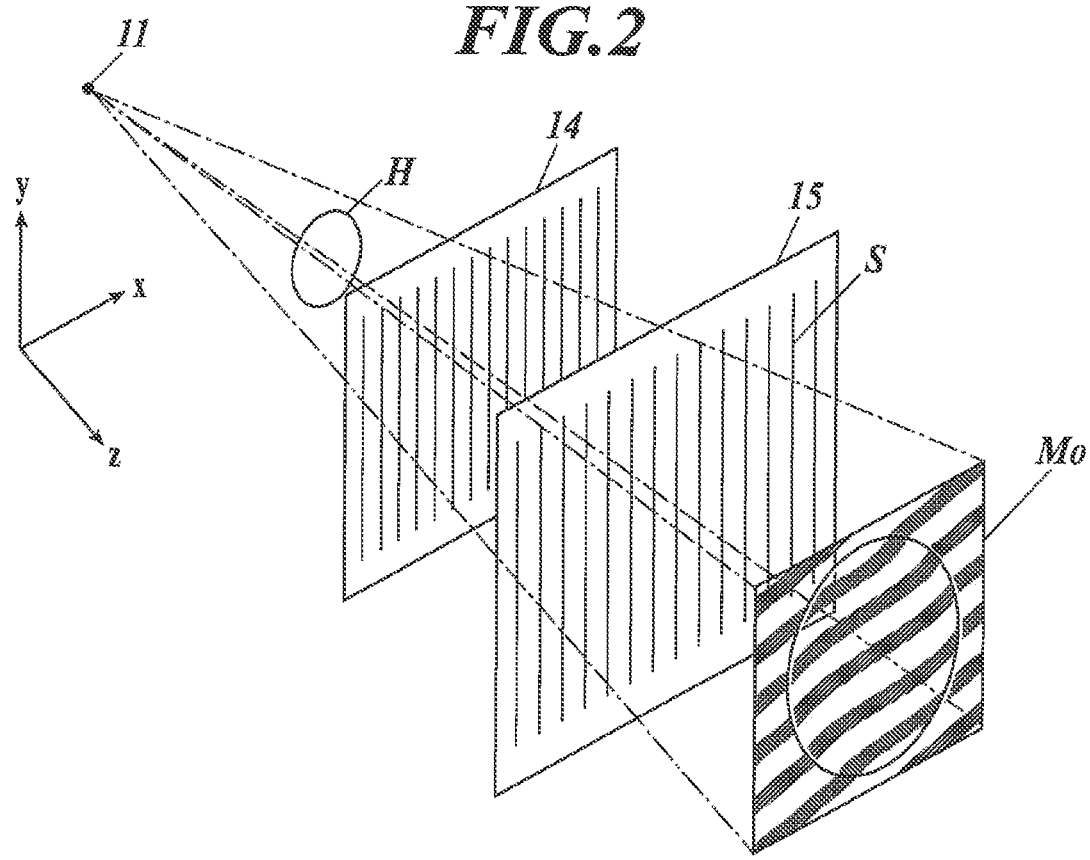
FIG. 2 is a diagram to explain principles of Talbot interferometers according to one or more embodiments of the present invention.

Although FIG. 2 shows the case of Talbot interferometer(s), the same explanation applies to the case of Talbot-Lau interferometers, basically. The z direction shown in FIG. 2 corresponds to the vertical direction in the X-ray Talbot imaging device 1 shown in FIG. 1, and the x and y directions shown in FIG. 2 correspond to the horizontal directions (front-back direction and right-left direction) in the X-ray Talbot imaging device 1 shown in FIG. 1.

Figure 3:
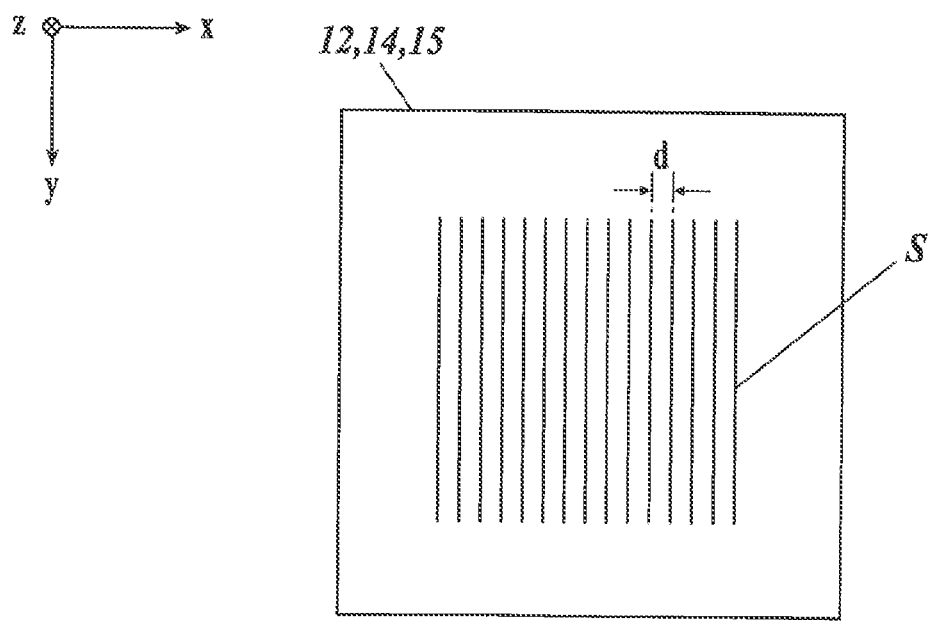
FIG. 3 is a schematic plan view of a source grating, a first grating and a second grating according to one or more embodiments of the present invention.

As shown in FIG. 3, in the first grating 14 and the second grating 15 (in the source grating 12 too in the case of a Talbot-Lau interferometer), slits S are arranged and formed at intervals of a predetermined distance d (i.e. the slit interval) in the x direction orthogonal to the z direction that is an X-ray emission direction.

As shown in FIG. 3, when X-rays emitted from an X-ray source 11a (X-rays emitted from the X-ray source 11a and made by the source grating 12 (not shown in FIG. 3) to be X-rays as if they were emitted from a plurality of light sources in the case of a Talbot-Lau interferometer) have passed through the first grating 14, the X-rays having passed through the first grating 14 form an image at constant intervals in the z direction. This image is called a self-image (also called grating image or the like), and phenomenon of the self-image being formed at constant intervals in the z direction is called Talbot effect.

That is, the Talbot effect is, as described above, the phenomenon of the self-image being formed at constant intervals in a light traveling direction of coherent light, which occurs when the light has passed through the first grating 14, in which the slits S are arranged at intervals of the distance d as shown in FIG. 3.

As shown in FIG. 2, the second grating 15, in which the slits S are arranged as with the first grating 14, is arranged at a position where the self-image of the first grating 14 is formed. If the second grating 15 is arranged such that an extending direction of the slits S (i.e. the y axis direction in FIG. 2) of the second grating 15 is approximately parallel to the extending direction of the slits S of the first grating 14, a moire image Mo is generated on the second grating 15.

In FIG. 2, the moire image Mo is shown away from the second grating 15 because if the moire image Mo is shown on the second grating 15, the moire fringes and the slits S coexist thereon and become indistinguishable from one another. In reality, the moire images Mo are formed on the second grating 15 and on its downstream side. The moire image(s) Mo is captured by the X-ray detector 16 arranged immediately under the second grating 15.

If, as shown in FIG. 2, the subject H exists between the X-ray source 11a and the first grating 14 (i.e. on the subject table 13 in FIG. 1), the phase of the X-rays is shifted by the subject H, so that the moire fringes in the moire image Mo are deformed from the periphery of the subject H as the border. On the other hand, if, although it is not shown, no subject H exists between the X-ray source 11a and the first grating 14, the moire image(s) Mo of only the moire fringes without deformation appears. This is the principles of Talbot interferometers and Talbot-Lau interferometers.

On the basis of the principles, in the X-ray Talbot imaging device 1 of one or more embodiments of the present invention, as shown in FIG. 1 as an example, the second grating 15 is arranged in a second cover unit 130 at a position where the self-image of the first grating 14 is formed. Further, as described above, in one or more embodiments of the present invention, the X-ray detector 16 is arranged immediately under the second grating 15. This is because if the second grating 15 and the X-ray detector 16 are arranged away from one another, the moire image Mo (shown in FIG. 2) becomes blurred.

The second cover unit 130 is provided to protect the first grating 14, the second grating 15, the X-ray detector 16 and so forth from people or things bumping against or touching these.

Although not shown, in the X-ray detector 16, conversion elements that generate electric signals according to the emitted X-rays (i.e. according to the X-rays with which the X-ray detector 16 is irradiated) are arranged two-dimensionally (in a matrix). The X-ray detector 16 reads the electric signals generated by the conversion elements as image signals. In one or more embodiments of the present invention, the X-ray detector 16 captures the moire image(s) Mo, which is an image made of the X-rays formed on the second grating 15, as the image signals of the respective conversion elements.

In one or more embodiments of the present invention, the X-ray Talbot imaging device 1 captures a plurality of moire images Mo by the fringe scanning method. That is, the X-ray Talbot imaging device 1 of one or more embodiments of the present invention captures a plurality of moire images Mo while shifting the first grating 14 and the second grating 15 relative to one another in the x axis direction (i.e. the direction orthogonal to the extending direction of the slits S (y axis direction)) shown in FIG. 1 to FIG. 3.

The image processing device 2 receives the image signals of the moire images Mo from the X-ray Talbot imaging device 1, and performs image processing thereon, thereby generating reconstructed images of an absorption image(s), a differential phase image(s), a small angle scattering image(s) and so forth on the basis of the moire images Mo.

The X-ray Talbot imaging device 1 of one or more embodiments of the present invention has a not-shown moving device or the like to move the first grating 14 in the x axis direction a predetermined amount (distance) for each moire image Mo to be captured by the fringe scanning method. The X-ray Talbot imaging device 1 may be configured to move, instead of the first grating 14, the second grating 15 or both of them.

The X-ray Talbot imaging device 1 may be configured to capture only one moire image Mo with the relative position of the first grating 14 and the second grating 15 fixed, and the image processing device 2 may be configured to perform the image processing thereon to analyze this moire image Mo by the Fourier transform method or the like, thereby generating reconstructed images of an absorption image, a differential phase image and so forth.

If the above method is used, the X-ray Talbot imaging device 1 does not need the above-described moving device or the like. One or more embodiments of the present invention are applicable to an X-ray Talbot imaging device not having such a moving device.

Other components of the X-ray Talbot imaging device 1 of one or more embodiments of the present invention are described. In one or more embodiments of the present invention, the X-ray Talbot imaging device 1 is, what is called, a vertical type, and the X-ray generator 11, the source grating 12, the subject table 13, the first grating 14, the second grating 15 and the X-ray detector 16 are arranged in this order in the gravity direction that is the z direction. That is, in one or more embodiments of the present invention, the z direction is the direction of emission of X-rays (i.e. the X-ray emission direction) from the X-ray generator 11.

The X-ray generator 11 includes, as the X-ray source 11a, a Coolidge X-ray source, a rotating anode X-ray source or the like that is widely and generally used at medical sites. Another type of X-ray source can also be used. The X-ray generator 11 of one or more embodiments of the present invention emits X-rays from the focal point as cone beams. That is, the X-ray generator 11 emits X-rays such that the X-rays spread as they are away from the X-ray generator 11.

In one or more embodiments of the present invention, the source grating 12 is arranged under the X-ray generator 11. In one or more embodiments of the present invention, in order not to transmit vibrations of the X-ray generator 11 to the source grating 12, the vibrations being caused by rotation of the anode of the X-ray source 11a or the like, the source grating 12 is not attached to the X-ray generator 11 but is attached to a fixing member 18a attached to the base 18 on the pole 17.

In one or more embodiments of the present invention, in order not to propagate the vibrations of the X-ray generator 11 to other components, such as the pole 17, of the X-ray Talbot imaging device 1 (or in order to make the vibrations to be propagated smaller), a buffer member 17a is arranged between the X-ray generator 11 and the pole 17.

In one or more embodiments of the present invention, to the above-described fixing member 18a, in addition to the source grating 12, a filtration filter (also called added filter) 112 to change the quality of the X-rays having passed through the source grating 12, an irradiation field aperture stop 113 to reduce the irradiation field to be irradiated with the X-rays, and an irradiation field lamp 114 to emit not X-rays but visible light to the subject H, thereby irradiating the subject H, for positioning before X-ray emission are attached, for example.

The source grating 12, the filtration filter 112 and the irradiation field aperture stop 113 do not need to be arranged in this order. Further, in one or more embodiments of the present invention, a first cover unit 120 is arranged in such a way as to contain the source grating 12 and so forth to protect them.

As shown in FIGS. 4A and 4B, the source grating 12, the first grating 14 and the second grating 15 are held by grating holders 12a, 14a and 15a, respectively, which hold the gratings 12, 14 and 15, respectively, along the horizontal directions. In order to move the first grating 14 or the second grating 15 during imaging by the fringe scanning method, the grating holder 14a or 15a itself is operated to move the first grating 14 or the second grating 15.

The subject table 13 is provided with a fixing unit (not shown) that fixes the position of the subject H with respect to the X-rays emitted from the X-ray generator 11. The fixing unit includes: a fixing part that can fixe the subject H at a predetermined position; and a movement mechanism that can move the fixing part on a predetermined curve in a plane which is approximately orthogonal to the X-ray emission direction (z direction). Use of this fixing unit makes it possible for the X-ray Talbot imaging device 1 to accurately image the same site of the subject H multiple times at different subject set angles. If a finger joint part is the subject H, the fixing part is provided with a finger holding member that can hold the finger and fixe its position and also can pull the finger to extend a space between the thorax side and the periphery side of the joint part. In one or more embodiments of the present invention, the subject set angle of the subject H is adjusted by the movement mechanism of the fixing unit. Alternatively, a configuration to continuously image the subject H in multiple directions by rotating the X-ray source 11a, the gratings 12, 14 and 15 (or grating holders) and the X-ray detector 16 around the subject table 13 may be adopted.

The subject set angle is an angle of the subject H in the horizontal directions relative to a grating direction(s) of the gratings 12, 14 and 15 (the extending direction of the slits S). The X-ray transmission amount varies according to the subject set angle, and the visible image in the reconstructed image generated from the X-rays varies according to the angle. Imaging the same site of the subject H multiple times at different subject set angles makes it possible to obtain, for each subject set angle, an image set constituted of three types of reconstructed images based on the same moire image(s) Mo having the subject set angle, and enables accurate diagnosis of the subject H accordingly.

[Image Processing Device]

Figure 5:
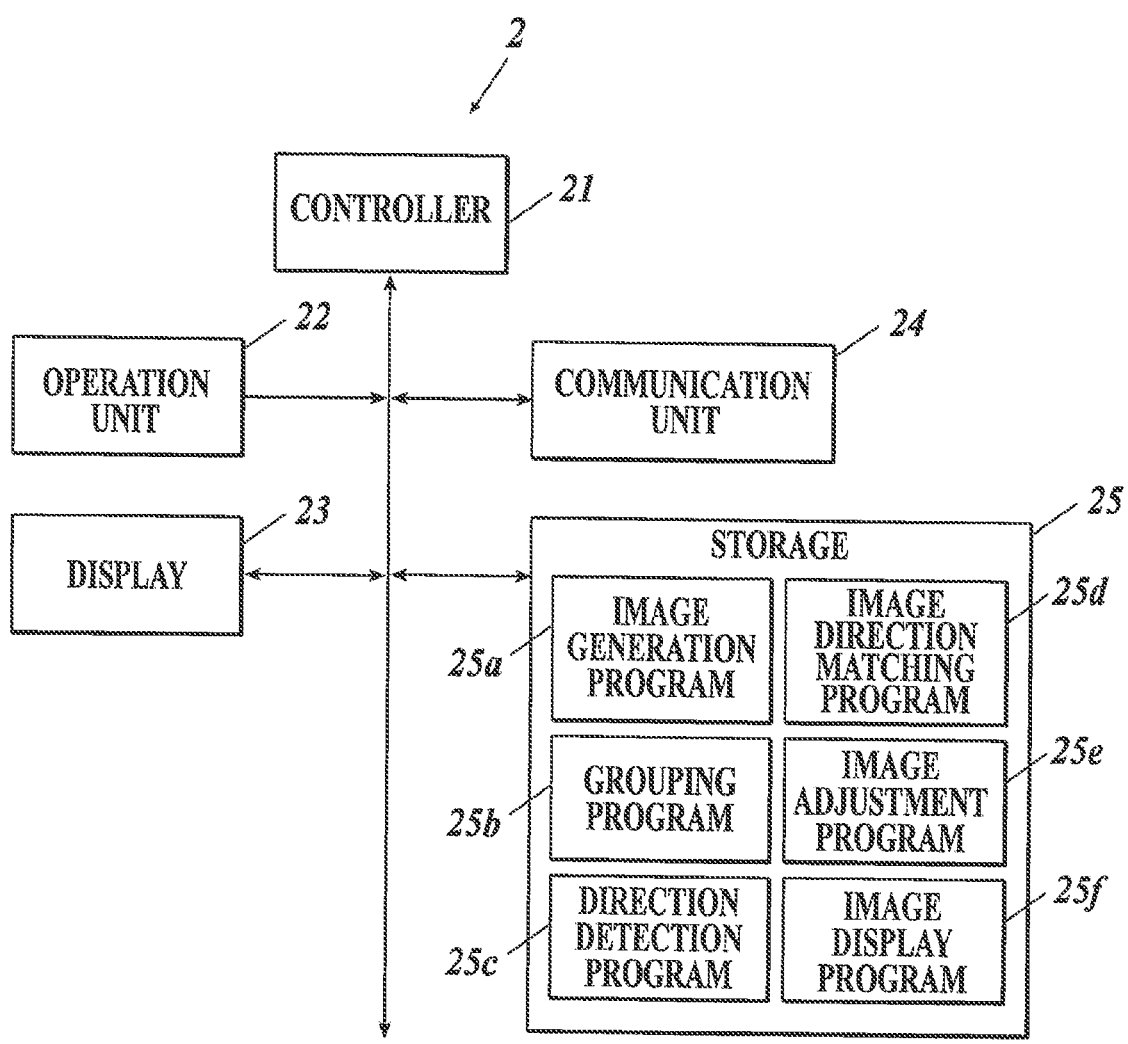
FIG. 5 is a block diagram showing functional configuration of an image processing device according to one or more embodiments of the present invention.

The image processing device 2 generates three types of high-resolution reconstructed images (absorption images, differential phase images and small angle scattering images) of the subject H, using the moire images Mo obtained by the X-ray Talbot imaging device 1, and also performs the image processing on the obtained reconstructed images. The image processing device 2 includes, as shown in FIG. 5, a controller 21, an operation unit 22, a display 23, a communication unit 24 and a storage 25.

The controller 21 includes a CPU (Central Processing Unit, hardware processor) and a RAM (Random Access Memory) and performs a variety of processing including the below-described image generation process in cooperation with programs stored in the storage 25.

The operation unit 22 includes: a keyboard having cursor keys, number input keys, various function keys and so forth; and a pointing device, such as a mouse, and outputs press signals of the keys of the keyboard and operation signals of the mouse to the controller 21 as input signals. The operation unit 22 may have a touchscreen integrated into a monitor of the display 23, and generate operation signals corresponding to operations thereon and output the signals to the controller 21.

Figure 9:
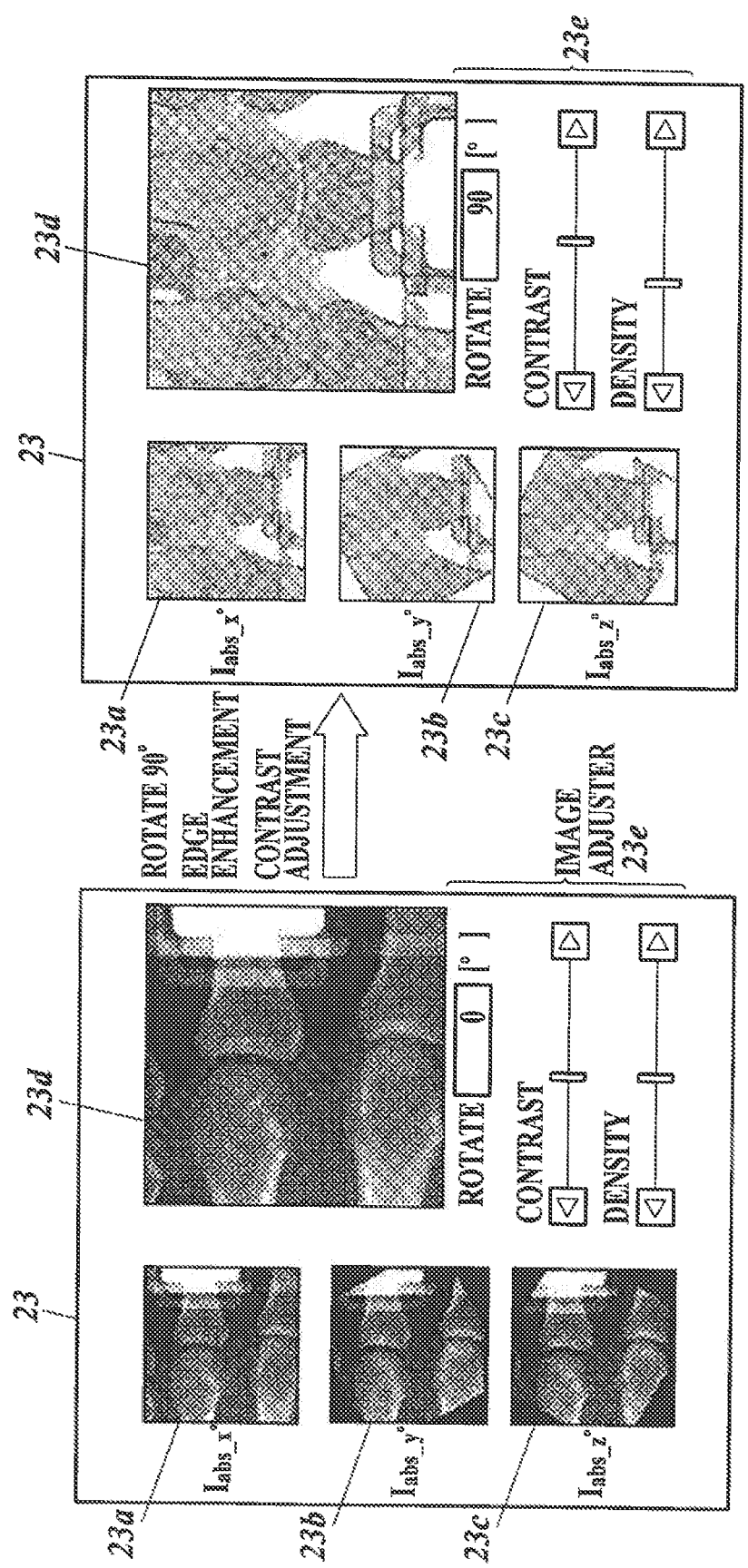
FIG. 9 shows a screen displayed on a display according to one or more embodiments of the present invention.

The display 23 includes the monitor, such as a CRT (Cathode Ray Tube) or an LCD (Liquid Crystal Display), and displays operation screens, operational statuses of the X-ray Talbot imaging device 1, the generated reconstructed images and so forth under display control of the controller 21. FIG. 9 shows a screen that is displayed on the display 23. On the screen, there are displayed a plurality of small windows 23a, 23b and 23c where the reconstructed images are displayed, a display window 23d where one reconstructed image selected from among the reconstructed images displayed in the small windows 23a, 23b and 23c is displayed, and an image adjuster 23e for an image adjustment process.

The communication unit 24 includes a communication interface, and communicates with the X-ray Talbot imaging device 1 and external systems, such as a PACS (Picture Archiving and Communication System), which are on a communication network, by wire or wirelessly.

The storage 25 stores therein the programs that are executed by the controller 21 and data necessary for execution of the programs. The storage 25 also stores therein basic information, such as an imaging date, a patient name and subject information (a diagnostic target site (imaging site) or information on a diagnostic target site and a disease name to be diagnosed on the site) in such a way as to be linked with the moire images Mo captured by the X-ray Talbot imaging device 1 and/or the reconstructed images generated by the image processing device 2.

The image processing that is executed on the basis of the programs stored in the storage 25 includes the image generation process, a grouping process, a direction detection process, an image direction matching process, the image adjustment process and an image display process.

The image generation process is performed by the controller 21 in cooperation with an image generation program 25a stored in the storage 25. More specifically, the controller 21 generates three types of reconstructed images using moire images Mo captured by the X-ray Talbot imaging device 1. Because the subject H is imaged at multiple subject set angles (in one or more embodiments of the present invention, for example, three angles of x°, y° and z°) as described above, the controller 21 generates three types of reconstructed images having each of the subject set angles different from one another.

Figure 6:
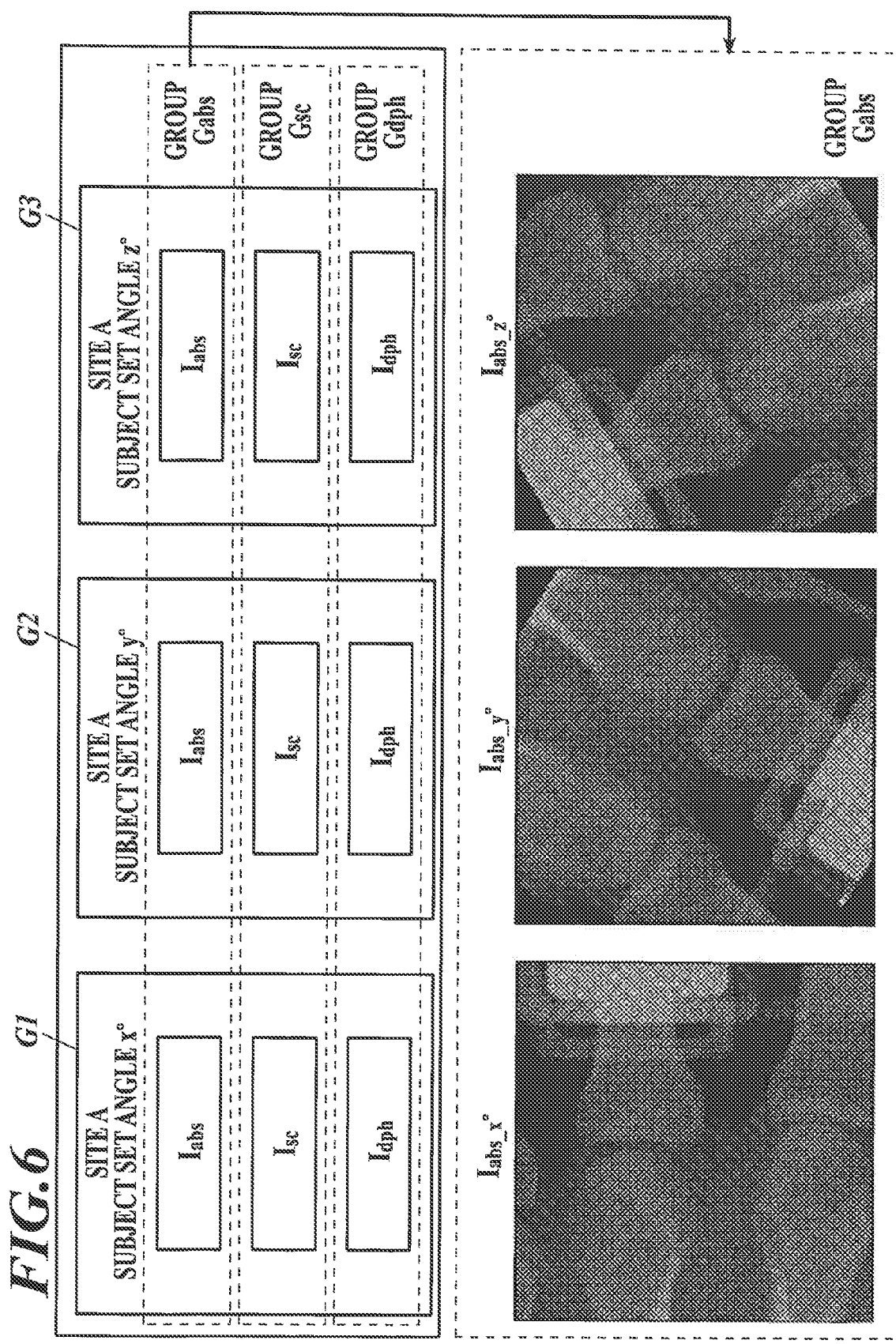
FIG. 6 is a diagram to explain operations of a controller of the image processing device in a grouping process according to one or more embodiments of the present invention.

The grouping process is performed by the controller 21 in cooperation with a grouping program 25b stored in the storage 25. More specifically, as shown in FIG. 6, the controller 21 groups the three types of reconstructed images by subject set angle (x°, y°, z°), and also groups the three types of reconstructed images by type (absorption image, differential phase image, small angle scattering image).

The groups by subject set angle are a first group G1 containing three types of reconstructed images having a subject set angle of x°, a second group G2 containing three types of reconstructed images having a subject set angle of y°, and a third group G3 containing three types of reconstructed images having a subject set angle of z°. That is, image sets each constituted of three types of reconstructed images generated on the basis of the same moire images Mo obtained by imaging the subject H at one angle are the groups by subject set angle (x°, y°, z°).

The groups by type are an absorption image group Gabs containing absorption images in the first, second and third groups G1, G2, G3, a differential phase image group Gdph containing differential phase images in the first, second and third groups G1, G2, G3, and a small angle scattering image group Gsc containing small angle scattering images in the first, second and third groups G1, G2, G3. That is, the three types of reconstructed images in the image sets obtained by imaging the same site of the subject H at angles of x°, y° and z° are classified into a group of absorption images, a group of differential phase images and a group of small angle scattering images.

In FIG. 6 to FIG. 9, the "$I_{abs}$" represents an absorption image, the "$I_{dph}$" represents a differential phase image, and the "$I_{sc}$" represents a small angle scattering image. Further, the "$I_{abs\_x}°$" represents an absorption image having a subject set angle of x°, the "$I_{abs\_y}°$" represents an absorption image having a subject set angle of y°, and the "$I_{abs\_z}°$" represents an absorption image having a subject set angle of z°.

The image processing device 2 can set imaging conditions in X-ray Talbot imaging for the X-ray source 11a. That is, the imaging conditions in X-ray Talbot imaging, such as a tube voltage, a tube current and an emission duration (or emission mAs value) for the X-ray source 11a and a filter type of the filtration filter 112 to be used, can be set on the image processing device 2. The settings of the image conditions can be linked and stored in advance with condition keys provided for operating the image processing device 2. In one or more embodiments of the present invention, the image sets to be grouped by type can also be specified by presses on condition keys on the image processing device 2. However, the present invention is not limited thereto, and each time imaging is performed, a user may determine whether to specify the image set as one of the image sets to be grouped by type.

The direction detection process is performed by the controller 22 in cooperation with a direction detection program 25c stored in the storage 25. More specifically, the controller 21 detects, in each of the three types of reconstructed images, the grating direction of the gratings 12, 14 and 15 and the subject set angle relative to the grating direction.

Detection of the grating direction by the direction detection process is based on images of markers 14b appearing in each of the three types of reconstructed images. The markers 14b are for determining the grating direction of the gratings 12, 14 and 15. Portions where the markers 14b are present as shown in FIG. 4A are less permeable to X-rays, and X-rays pass through the surroundings (grating holder 14a), so that the images of the markers 14b appear in each of the reconstructed images. The portions where the markers 14b are present may be made to be more permeable to X-rays and the surroundings (grating holder 14a) may be made to be less permeable to X-rays so that the images of the markers 14b can appear in each of the reconstructed images. Alternatively, notched makers 14c may be formed in the grating holder 14a as shown in FIG. 4B so that convex images can appear in each of the reconstructed images.

In one or more embodiments of the present invention, as shown in FIG. 4A, the markers 14b are placed on the grating holder 14a that holds the first grating 14. For example, if the grating direction of the first grating 14 is the y direction, the markers 14b are placed at both end parts in the x direction, which is orthogonal to the grating direction. When the X-ray Talbot imaging device 1 images the subject H, the images of the makers 14b appear in the moire images Mo. If the images of the markers 14b appear in the moire images Mo, the images of the markers 14b appear in the reconstructed images generated on the basis of the moire images Mo. This makes it possible to readily determine the grating direction of the gratings 12, 14 and 15.

In one or more embodiments of the present invention, the markers 14b are placed on the grating holder 14a that holds the first grating 14 as described above. However, the present invention is not limited thereto. For example, the markers 14b may be placed on the grating holders 12a and/or 15a that hold the gratings 12 and 15, respectively, may be placed on the gratings 12, 14 and/or 15 themselves, or may be placed on the fixing unit that fixes the position of the subject H. Further, in one or more embodiments of the present invention, the markers 14b are placed at points in the direction orthogonal to the grating direction, but may be placed at points in the direction parallel to the grating direction.

The grating direction may be detected and determined without using the markers 14b, for example, by making the shape(s) of the grating(s) anisotropic (e.g. rectangular). That is, if the shape of the grating is anisotropic, the captured moire images Mo are anisotropic and the three types of reconstructed images are also anisotropic, so that the grating direction can be determined.

Detection of the subject set angle by the direction detection process is based on the subject set angle (i.e. a subject set angle of x°, y° or z°) linked and stored in advance with the condition key described above.

The present invention is not limited thereto, and the subject set angle may be detected anatomically on the basis of each generated reconstructed image. That is, the subject set angle may be detected by analyzing a subject image in each reconstructed image on the basis of information on the structure of the human body. Because the site to be imaged is the same, the subject set angle can be readily determined if a part specific to the site is in the reconstructed image(s).

Additionally or alternatively, a subject direction marker(s) (not shown) to determine the direction of the subject H may be placed on the subject H itself or the fixing unit described above. The subject direction marker is not particularly limited as far as it can make an image made of the X-ray transmission amount different from that of the subject H appear in each reconstructed image. For example, a patch(es) made of metal is used.

Alternatively, an angle input by a user may be regarded as the subject set angle (x°, y°, z°).

Figure 7:
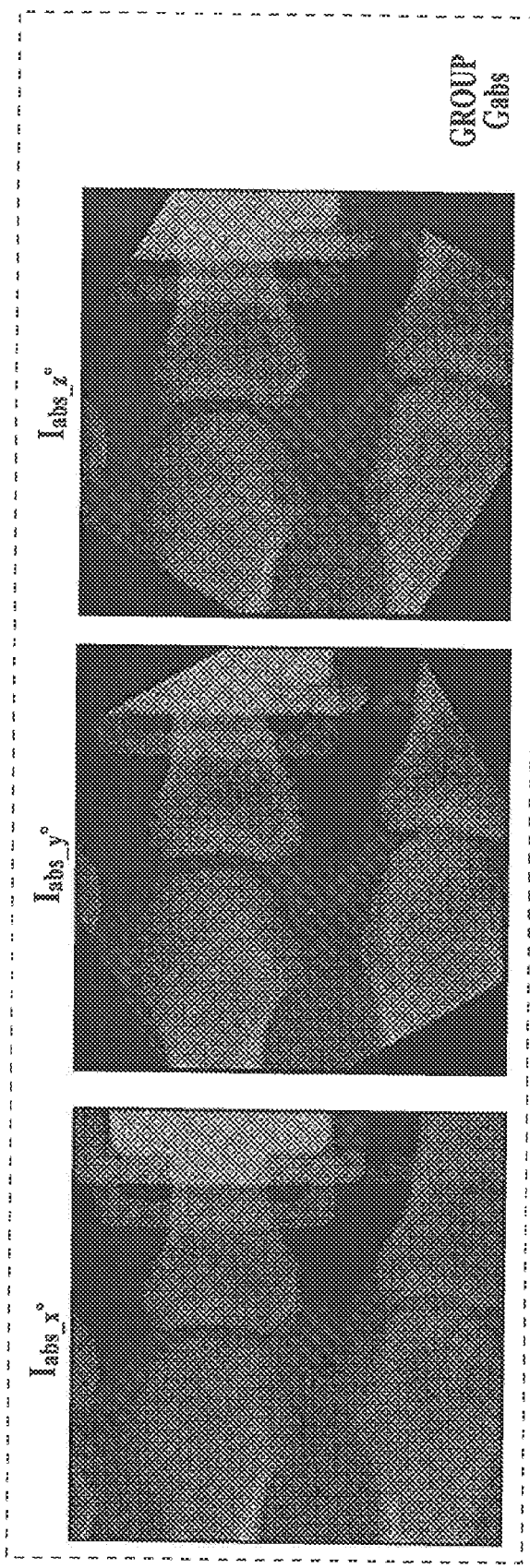
FIG. 7 is a diagram to explain operations of the controller of the image processing device in an image direction matching process according to one or more embodiments of the present invention.

The image direction matching process is performed by the controller 21 in cooperation with an image direction matching program 25d stored in the storage 25. More specifically, the image directions (i.e. subject directions) are matched with a reference direction on the basis of the detected grating direction(s) and the subject set angles in the reconstructed images of a group as shown in FIG. 7.

If the human body is imaged, the reference direction with which the image directions are matched is basically determined according to the site to be imaged. The reference directions for the respective imaging sites are stored in the storage 25 as a reference direction setting information list. The reconstructed images of a group(s) are corrected such that their image directions match the reference direction written in the list for the site of the subject H. However, the present invention is not limited thereto, and the image directions may be corrected on the basis of past imaging information. For example, if the same site of a patient (the same patient) is imaged regularly, the image directions in the reconstructed images are corrected on the basis of the past imaging information. Alternatively, the reference direction may be a direction specified by a user. If the image directions in the reconstructed images are matched with one another, the direction of the subject H in the reconstructed image generated first may be regarded as the reference direction, or the direction of the subject H in an image captured at a predetermined subject set angle may be regarded as the reference direction.

Figure 8:
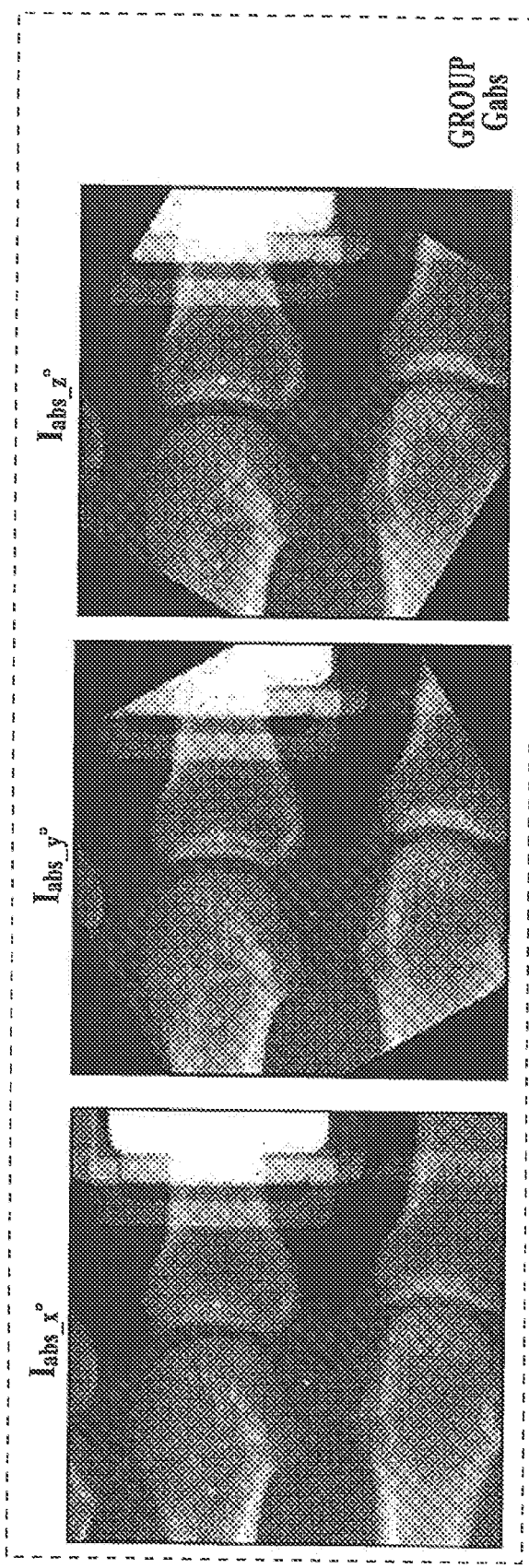
FIG. 8 is a diagram to explain operations of the controller of the image processing device in an image adjustment process according to one or more embodiments of the present invention.

The image adjustment process is performed by the controller 21 in cooperation with an image adjustment process program 25e stored in the storage 25. More specifically, the same image adjustment process is performed on the reconstructed images of a group(s) as shown in FIG. 8. After the image adjustment process, the images are output to the display 23. Examples of the image adjustment process include image rotation, enlargement/reduction, image trimming, contrast adjustment and image frequency processing.

The reconstructed images after the image direction matching process are displayed in display windows of a certain size(s) (e.g. the small windows 23a, 23b and 23c (and the display window 23d)). At the time, if a same-size display mode is performed to display the reconstructed images of a group(s) with the same subject size, the reconstructed image(s) having the subject size larger than the display window(s) is reduced by reduction of the enlargement/reduction, and the reconstructed images of the group are reduced at a reduction ratio of the most reduced reconstructed image in the group and output.

The image trimming may be performed on the reconstructed image(s) having the subject size larger than the display window(s) to display the reconstructed images of the group with the same subject size, namely, to display the reconstructed images in the same-size display mode. Consequently, the reconstructed image(s) with the part(s) protruding from the display window(s) cut can be output. The reconstructed image(s) having the part(s) protruding from the display window(s) may occurs, for example, by enlargement of the enlargement/reduction or the image rotation.

The contrast adjustment adjusts contrast in the reconstructed images. That is, the contrast adjustment adjusts a light-dark ratio of each reconstructed image.

The image frequency processing removes noise from the reconstructed images and improves image quality accordingly.

The reconstructed images grouped by type shown in FIG. 8 are the reconstructed images grouped by type shown in FIG. 7 and subjected to the image adjustment process.

In one or more embodiments of the present invention, on the grouped reconstructed images having different subject set angles, a variety of types of image adjustment is performed by the above image adjustment process. Further, in order to emphasize a part(s) that a user(s) would like to view, inter-image operation may be performed on the reconstructed images. This inter-image operation may be included in the image adjustment process.

More specifically, inter-image operation images generated by the inter-image operation are generated by a variety of mathematical operations after positioning of the reconstructed images. That is, the image directions in the reconstructed images of a group having different subject set angles, the reconstructed images being images before the inter-image operation, are matched with one another, and the inter-image operation is performed on the reconstructed images, so that the inter-image operation image(s) is generated. The inter-image operation image(s) is displayed on the screen where the reconstructed images are displayed. The inter-image operation images include: an image generated by obtaining difference(s) between the reconstructed images having different subject set angles so as to leave only the part(s) that a user would like to view; and an image generated by adding up all the reconstructed images having different subject set angles so as to emphasize the part(s) that a user would like to view. The inter-image operation image(s) obtained by the inter-image operation may be additionally registered into the group of the reconstructed images from which the inter-image operation image(s) is generated and be displayed on the display 23.

Far more specifically, the inter-image operation image obtained by evenly adding up all the images of the same type has increased information on tissues of the site A as the subject H, so that the part(s) that a user would like to view is emphasized.

Alternatively or additionally, an image (inter-image operation image) in which all the tissues of the site A as the subject H are visible and a target tissue(s) thereof is emphasized is obtained by weighting the reconstructed images according to their subject set angles and adding up the weighted reconstructed images. For example, if, among the reconstructed images, there is a reconstructed image in which an image in a direction that a user would like to view is more emphasized, but a part(s) unnecessary for the user appears in the emphasized image in the reconstructed image having a subject set angle, the inter-image operation is performed on the reconstructed image and a reconstructed image having another subject set angle, so that the part(s) unnecessary for the user is reduced from the image, and the inter-image operation image in which the image that the user would like to view is more visible can be obtained. The inter-image operation image obtained by weighting the reconstructed images and then performing the inter-image operation on the weighted reconstructed images may be displayed on the display 23.

The inter-image operation image in which the target tissue of the site A as the subject H is emphasized can be obtained by subtracting the reconstructed images having different subject set angles from one another.

The image display process is performed by the controller 21 in cooperation with an image display program 25f stored in the storage 25. More specifically, the controller 21 causes the display 23 to display the reconstructed images grouped by subject set angle or the reconstructed images grouped by type as shown in FIG. 9. The reconstructed images to be displayed have been subjected to the image adjustment process.

On the screen of the display 23, as shown in FIG. 9, the small windows 23a, 23b and 23c, the display window 23d and the image adjuster 23e are displayed. All the reconstructed images of a group(s) are displayed in line on the same screen. That is, the reconstructed images of the group are displayed in the small windows 23a, 23b and 23c that are arranged in line. The sizes of the images to be displayed on the screen may be not the same, and hence the display window 23d is set to be larger than the small windows 23a, 23b and 23c. The above image adjustment process (or the image adjustment) can also be performed on the displayed reconstructed images, and the image adjustment process performed on one of the displayed reconstructed images is reflected on all of the displayed reconstructed images.

On the displayed reconstructed images or the screen, information on the grating direction(s) and information on the subject set angle(s) may be displayed. Further, displaying the reconstructed images grouped by type and displaying the reconstructed images grouped by subject set angle (x°, y°, z°) may be switched. Still further, in order to perform the image adjustment, separately or individually, on the reconstructed images that are first displayed after the image adjustment process, a switching system that can release the image adjustment process to be performed on all of the displayed images simultaneously may be adopted.

[Image Processing by Image Processing Device]

Next, one or more embodiments of the image processing that is performed by the image processing device 2 of the X-ray imaging system configured as described above are described.

Before the image processing device 2 performs the image processing, the X-ray Talbot imaging device 1 images the subject H. At the time, the X-ray Talbot imaging device 1 images the same site A of the subject H multiple times at different subject set angles. In one or more embodiments of the present invention, the X-ray Talbot imaging device 1 images the subject H in three directions (angles) of x°, y° and z°. Imaging in this way generates the moire images Mo having three subject set angles of x°, y° and z°. In the moire images Mo, the images of the markers 14b appear.

After the X-ray Talbot imaging device 1 images the subject H at subject set angles of x°, y° and z°, thereby obtaining the moire images Mo, the image processing device 2 performs the image processing.

When the image processing device 2 performs the image processing, the controller 21 of the image processing device 2 first generates, for the respective subject set angles of x°, y° and z°, three types of reconstructed images (absorption images, differential phase images and small angle scattering images) on the basis of the moire images Mo having the subject set angles of x°, y° and z° obtained by the X-ray Talbot imaging device 1. That is, the controller 21 performs the image generation process on the basis of the image generation program 25a, thereby obtaining three types of reconstructed images (an absorption image, a differential phase image and a small angle scattering image) having a subject set angle of x°, three types of reconstructed images (an absorption image, a differential phase image and a small angle scattering image) having a subject set angle of y°, and three types of reconstructed images (an absorption image, a differential phase image and a small angle scattering image) having a subject set angle of z°.

Next, the controller 21 groups the obtained three types of reconstructed images by subject set angle (x°, y°, z°), and also groups the obtained three types of reconstructed images by type (absorption image, differential phase image, small angle scattering image). That is, the controller 21 classifies the three types of reconstructed images having the subject set angles obtained by the image generation process into subject set angle groups, namely, the first group G1, which is a subject set angle x° group, the second group G2, which is a subject set angle y° group, and the third group G3, which is a subject set angle z° group, and also into type groups, namely, the absorption image group Gabs, the differential phase image group Gdph and the small angle scattering image group Gsc.

Next, among the groups G1, G2, G3, Gabs, Gdph, Gsc, the reconstructed images of the group(s) Gabs, Gdph, Gsc (or G1, G2, G3) to be displayed on the display 23 are input into the controller 21, and the controller 21 detects, in each reconstructed image of the group Gabs, Gdph, Gsc (or G1, G2, G3), the grating direction and the subject set angle (x°, y°, z°) relative to the grating direction.

Next, the controller 21 corrects each reconstructed image of the group Gabs, Gdph, Gsc (or G1, G2, G3) to be displayed on the display 23 on the basis of the detected grating direction and the detected subject set angle (x°, y°, z°) such that the image direction matches the reference direction (i.e. performs the image direction matching process on the reconstructed images).

Next, the controller 21 performs the image adjustment process on the reconstructed images of the group Gabs, Gdph, Gsc (or G1, G2, G3) subjected to the image direction matching process. That is, the controller 21 performs the above-described image rotation, enlargement/reduction, image trimming, contrast adjustment, image frequency processing and/or the like on the reconstructed images of the group Gabs, Gdph, Gsc (or G1, G2, G3) subjected to the image direction matching process. Then, the controller 21 outputs the reconstructed images of the group Gabs, Gdph, Gsc (or G1, G2, G3) subjected to the image adjustment process to the display 23.

On the display 23, the small windows 23a, 23b and 23c, the display window 23d and the image adjuster 23e are displayed. In the small windows 23a, 23b and 23c, the reconstructed images of the group Gabs, Gdph, Gsc (or G1, G2, G3) subjected to the image adjustment process are displayed. In the display window 23d, one image selected from among the reconstructed images of the group Gabs, Gdph, Gsc (or G1, G2, G3) subjected to the image adjustment process is displayed in an enlarged display mode.

The image adjustment process performed on one of the reconstructed images displayed in the small windows 23a, 23b and 23c and the display window 23d is reflected on all of the displayed reconstructed images. On the left side in FIG. 9, the reconstructed images subjected to the image adjustment process are displayed, whereas on the right side in FIG. 9, the reconstructed images, displayed on the left side in FIG. 9, further subjected to image rotation of 90°, edge enhancement and contrast adjustment are displayed.

Thus, the image processing device 2 performs the image processing on the images of the subject H captured by the X-ray Talbot imaging device 1. The image processing device 2 can perform the image processing on the reconstructed images grouped by subject set angle and the reconstructed images grouped by type in the same manner.

As described above, according to one or more embodiments of the present invention, the controller 21 generates, from the moire images Mo obtained by imaging of the same site A of the subject H multiple times at different subject set angles, multiple types of reconstructed images having the different subject set angles; groups the reconstructed images; detects the grating direction and the subject set angle in each reconstructed image; rotates each reconstructed image such that the direction of an image (the subject H in the reconstructed image) matches the reference direction; and performs the same image adjustment process on the grouped reconstructed images. This makes it possible to display the reconstructed images of the same site A of the subject H having different subject set angles in line such that their subject directions match with one another, and also makes it possible to perform the same image adjustment process for image quality or the like on all of the reconstructed images simultaneously. Consequently, the grouped reconstructed images can be adjusted with a small number of operations to the extent that diagnosis can be readily made. Thus, the X-ray imaging system is user-friendly and can increase diagnostic efficiency.

Further, the controller 21 detects the grating direction of the gratings 12, 14 and 15 in each of the three types of reconstructed images on the basis of the images of the markers 14b. This makes it possible to readily and accurately determine the grating direction of the gratings 12, 14 and 15 on the basis of the images of the markers 14*b*.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An X-ray imaging system comprising:
an X-ray Talbot imaging device comprising:
   an X-ray source;
   a plurality of gratings;
   a grating holder that holds the grating; and
   an X-ray detector disposed in line in an X-ray emission axis direction, wherein
the X-ray Talbot imaging device emits an X-ray from the X-ray source to the X-ray detector through a subject and the gratings, and takes an image of a same site of the subject multiple times at different subject set angles to capture, with the X-ray detector, moire images having the different subject set angles, wherein each of the subject set angles is an angle of the subject in a horizontal direction with respect to a grating direction of the gratings; and
an image processing device comprising a hardware processor and a display, wherein the hardware processor:
   generates multiple types of reconstructed images based on each of the moire images having the different subject set angles captured by the X-ray Talbot imaging device;
   groups the multiple types of the reconstructed images by each of the subject set angles, and groups the multiple types of the reconstructed images by each of the types;
   detects, in each of the multiple types of the reconstructed images, the grating direction and each of the subject set angles;
   rotates each of the grouped reconstructed images to match a subject direction of each of the grouped reconstructed images with a reference direction based on the detected grating direction and the detected subject set angle;
   performs an image adjustment process on the grouped reconstructed images;
   causes the display to display, side by side, the grouped reconstructed images of the same site of the subject captured at the different subject set angles, such that the subject directions of the grouped reconstructed images all match one another; and
   when performing the image adjustment process on one of the displayed reconstructed images, reflects the same image adjustment process in all the remaining displayed reconstructed images,
the grating holder includes a marker that determines the grating direction, the marker being more permeable or less permeable to X-ray than a portion of the grating holder other than the marker,
the X-ray Talbot imaging device captures the moire images and causes an image of the marker to appear in each of the multiple types of the reconstructed images, and
the hardware processor detects the grating direction in each of the multiple types of the reconstructed images based on the image of the marker.

2. The X-ray imaging system according to claim 1, further comprising:
a subject table that fixes the subject at a predetermined position and moves in place approximately orthogonal to the X-ray emission axis direction when the X-ray Talbot imaging device takes the image to capture the moire images having the different subject set angles.

3. The X-ray imaging system according to claim 1, further comprising:
a subject table that fixes the subject at a predetermined position, wherein
the X-ray Talbot imaging device rotates around the subject table when taking the image to capture the moire images having the different subject set angles.

4. The X-ray imaging system according to claim 1, wherein
the reconstructed images grouped by each of the subject set angles include three types of images: absorption image; differential phase image; and small angle scattering image.

5. The X-ray imaging system according to claim 1, wherein
the grating holder includes, as the marker, two markers disposed at both end parts of the grading holder in a direction orthogonal to the grating direction.

\* \* \* \* \*